US00PP11097P

United States Patent [19]

Sallin

[11] Patent Number: Plant 11,097

[45] Date of Patent: Oct. 19, 1999

[54] SOUTHERN LIVE OAK TREE NAMED 'CLTF2'

[75] Inventor: Michel Sallin, Clermont, Fla.

[73] Assignee: Cherry Lake Tree Farms, Inc., Groveland, Fla.

[21] Appl. No.: 09/002,357

[22] Filed: Jan. 2, 1998

[51] Int. Cl.[6] ..... A01H 5/00

[52] U.S. Cl. ..... Plt./225

[58] Field of Search ..... Plt./225

[56] References Cited

PUBLICATIONS

Thomas S. Elias, The Complete Trees of North America Field Guide and Natural History, Outdoor Life/Nature Books, New York, pp. 341–342, 1980.

*Primary Examiner*—Howard J. Locker
*Assistant Examiner*—Kent L. Bell
*Attorney, Agent, or Firm*—James A. Lucas

[57] ABSTRACT

A new Southern Live Oak of the *virginiana* species distinguished by its large dark green leaves, fast rate of growth, a central leader supported by strong secondary branching and thicker stem and twig caliper than that of the parent.

4 Drawing Sheets

BACKGROUND OF THE NEW PLANT

My new variety of *Quercus virginiana*, commonly called Southern Live Oak, was discovered by me in 1996. I have given my plant the variety name 'CLTF2'. Southern Live Oak trees from seed are extremely variable and often unpredictable in growth shapes, growth rates, leaf characteristics, bark characteristics and branching structure because of its ease in cross pollination with other Southern Live Oak cultivars.

My new variety was selected from a seedling crop of 25,000 acorns planted November 1992. These seeds were produced from open pollination. The seeds came from one specimen I have collected seed from for the past 12 years. After two years of grading, I made the selection of my new variety from a final group of 6,000 trees that had trunk calipers ranging from 4–5 inches. These trees were grown in my nursery in native soil under normal cultivation located in Groveland, Fla. In 1996, my attention was drawn to the new tree due to it having large dark green leaves, naturally occurring central leader with secondary branches having favorable strong branching attachment.

I have successfully reproduced this new variety of Southern Live Oak by means of grafting onto *Quercus virginiana* seedlings at my nursery in Groveland, Fla. This propagation, and successive asexual propagation by grafting, and observation of the resulting progeny, has proven the characteristics of my new variety of tree to be firmly fixed.

SUMMARY OF THE NEW PLANT

The major distinguishing characteristics that set this variety apart from other Southern Live Oak seedlings are:

1. larger — dark green leaves.
2. faster growth rate.
3. thicker trunk, branch and stem caliper.
4. dominant central leader with strong branching angles.

BRIEF DESCRIPTION OF THE DRAWINGS

The accompanying color photographs depict the distinguishing characteristics of my new Southern Live Oak variety, as nearly true as is reasonably possible to make the same in color illustrations of this character.

BOTANICAL DESCRIPTION OF THE NEW PLANT

Figure 1:
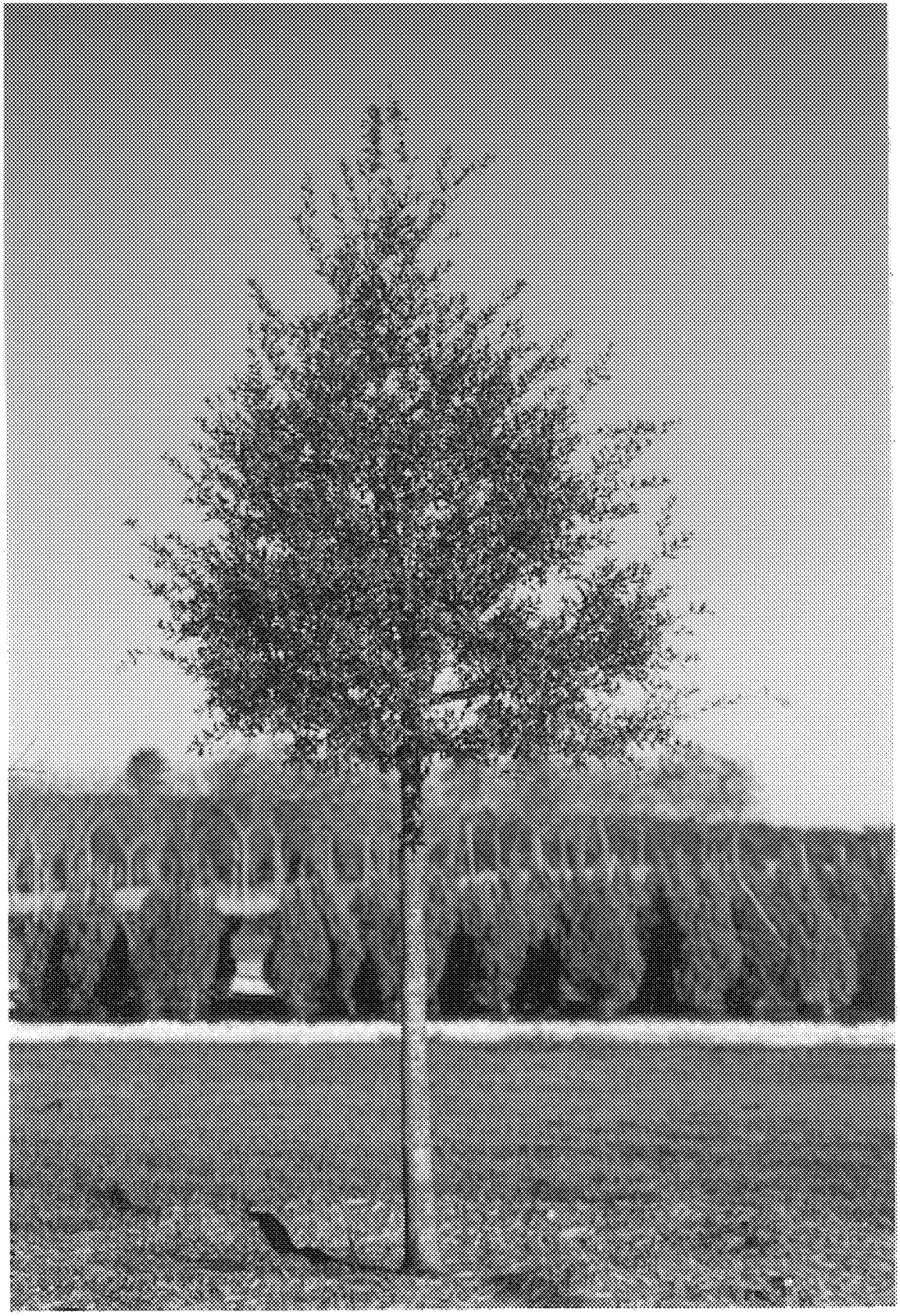
FIG. 1 illustrates the original five year old tree of the new variety that is 16 feet tall, 9 feet wide, with a caliper of 5 inches. This illustrates the prominent central leader, straight trunk and symmetrical canopy. Photograph taken in December.
Figure 2:
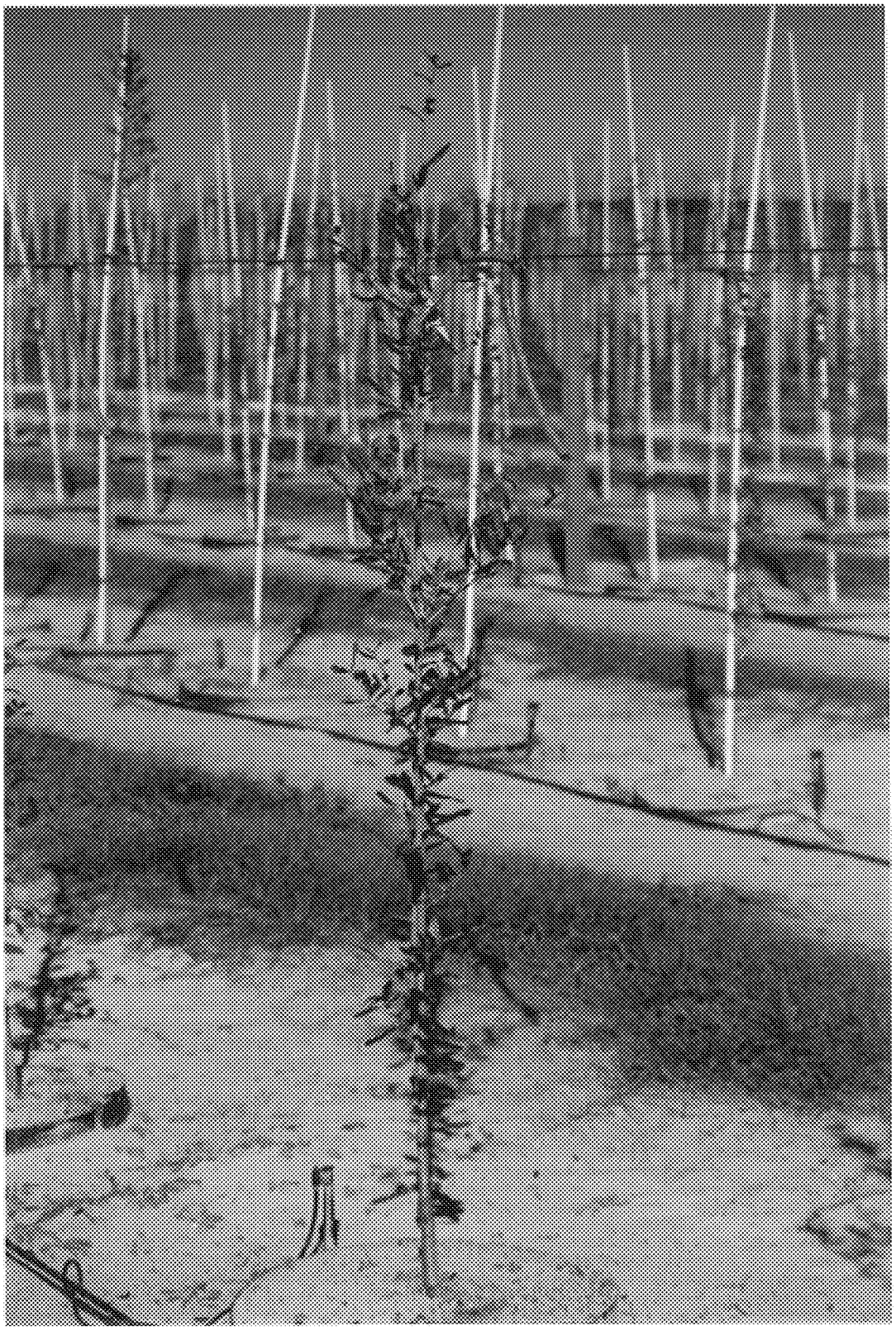
FIG. 2 shows a young grafted tree 5.5 feet tall after 4.5 months from when the graft "took". Also illustrated is the thick caliper of the lateral branches and the naturally growing central leader.
Figure 3:
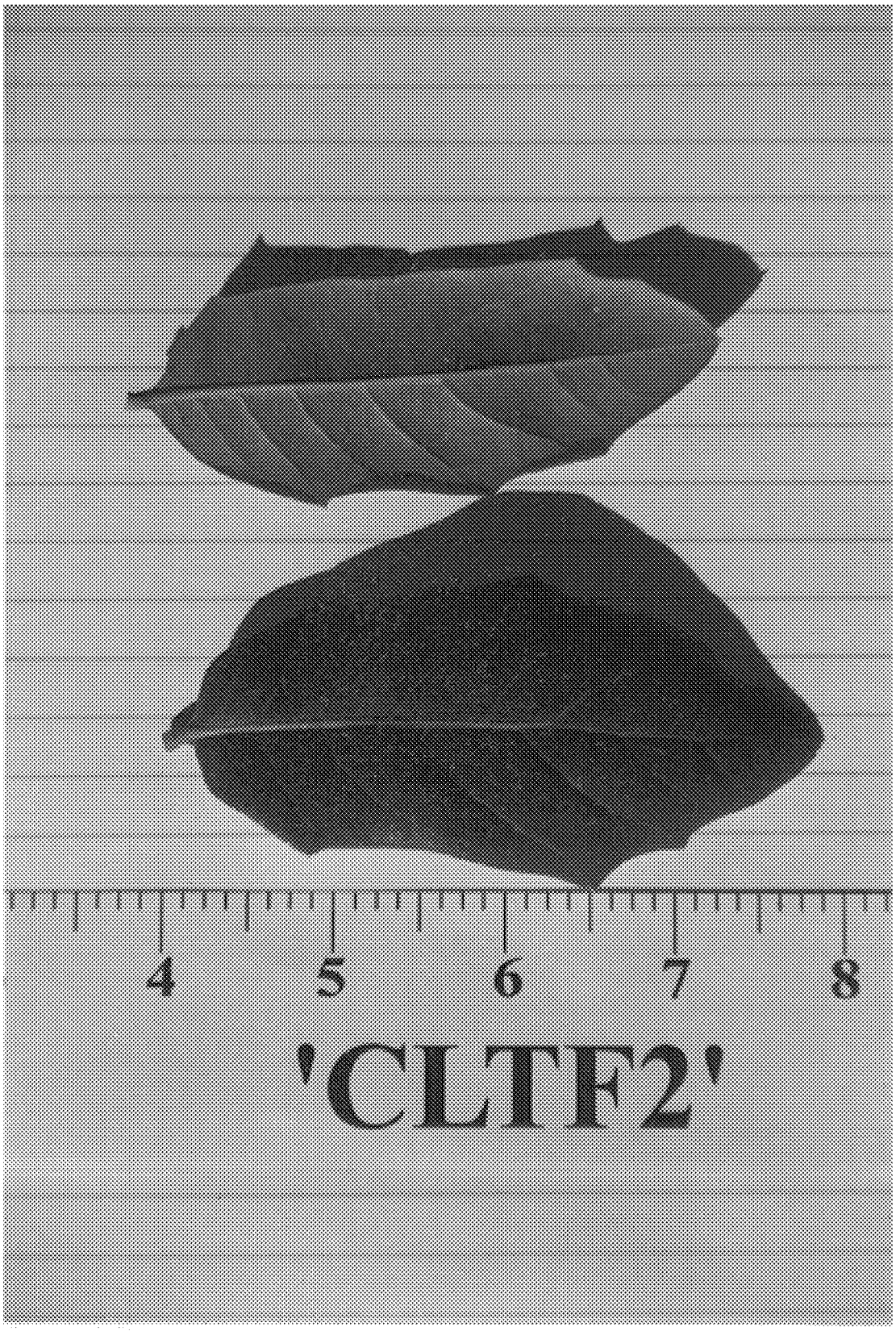
FIG. 3 shows the dark green leaves. The top leaf is the lower leaf surface, and the bottom leaf is upper leaf surface of the new variety. Photograph taken in December.
Figure 4:
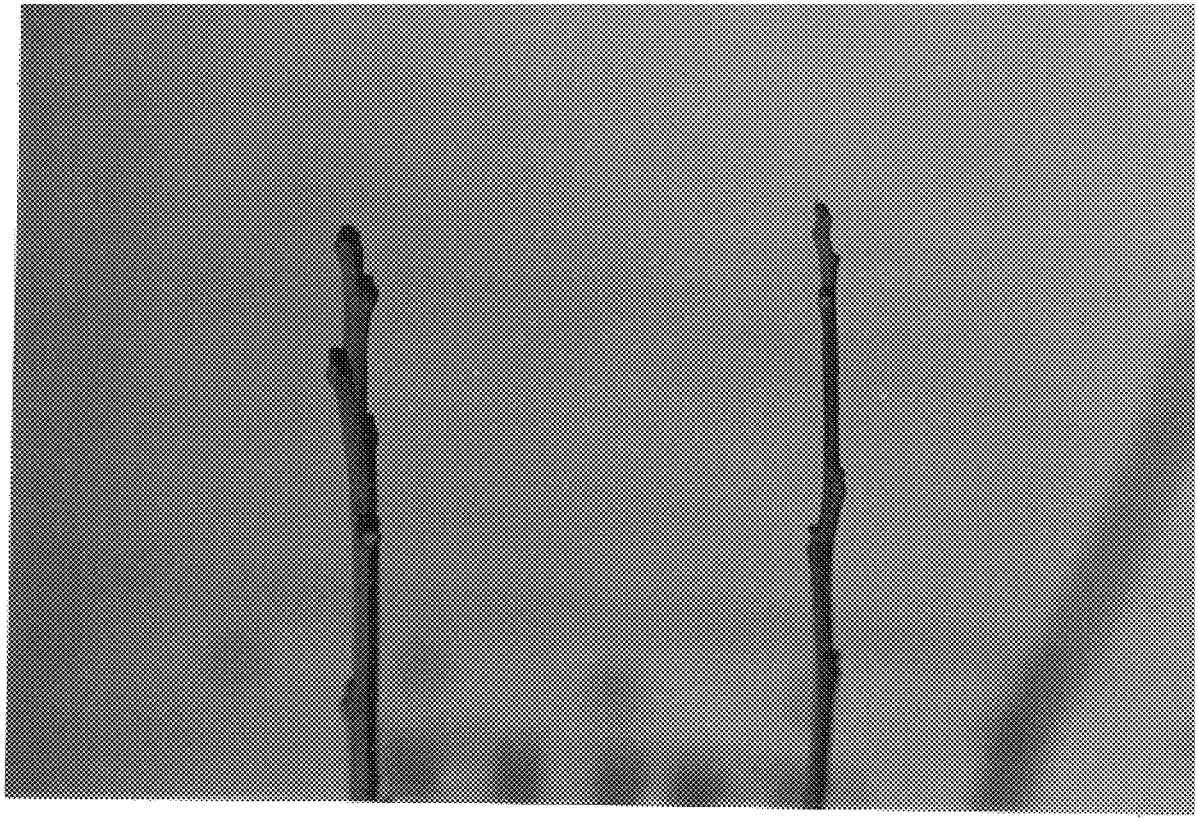
FIG. 4 illustrates on the left, thicker twig caliper this new variety develops, compared to the thin caliper of a typical seedling on the right.

My 'CLTF2' variety has not been observed under all growing conditions and thus variations may occur as a result of different growing conditions. The following is a detailed description of my new variety of Southern Live Oak, based upon observations from a tree growing at Cherry Lake Tree Farm. All color terminology is in accordance with The Royal Horticultural Society Colour Chart, published by The Royal Horticultural Society of London.

Origin: Seedling:

Parentage: The initial seedling originated through open pollination from an unpatented and unnamed cultivar of Southern Live Oak. The seed parent differs from the claimed tree in the shape, color and size of the leaves, the amount of twiggy growth, the color of the bark, the growth rate and seed. The leaf margins of the claimed tree are revolute but not undulating while the margins of the parent are undulating but not revolute. The upper surface of the leaves of the claimed tree is a darker green than the upper leaf surface of the seed parent. The leaf apices of the claimed tree are abruptly acuminate whereas the apices of the seed parent are obtuse. The claimed tree produces much less small twiggy growth than the parent tree. The claimed tree produces a spring and a fall flush of 18" to 24" as compared to a flush of 8" to 12" for the seed parent. The bark of the claimed tree is light brown and smooth while the bark of the seed parent is dark brown and rigid to flaky.

Classification:

*Botanic.*—*Quercus virginiana.*

*Commercial.*—Southern Luve Oak or Live Oak.

Propagation: Asexually using the grafting method onto *Quercus virginiana* seedlings.

Locality where grown and observed: Groveland, Fla.

Tree: Tall semi-evergreen tree. Oval growth habit with a single, straight and strong central trunk when young. Naturally maintains a dense habit because of its abundant scaffold branch development.

Bark: Trunk color on trees less than one year old is greyed green (R.H.S. 197C) with smooth texture. After 5 years the trunk begins to develop blocky and furrowed characteristics.

Height: My original new tree in a period of 5 years from seed reaches a height of 16 feet, with a spread of 9 feet and trunk caliper of 5 inches. Ultimate height is unknown.

Vigor and uniformity: Vigorous, being faster growing. Once the grafts "take", my new tree has grown 5½ feet in 4½ months with symmetrical scaffold branching structure, under my nursery conditions in Groveland, Fla. It would take a seedling of a different cultivar within the same species 9 to 12 months to equal that rate of growth.

Branching: My new tree maintains a dense framework of branches and leaves, producing a central leader through the canopy with strong lateral branching. The new growth ascends at a angle of 45 to 55 degrees. This angle increases to 75 to 85 degrees as the branch matures maaking for very strong branch attachment.

Leaves: Alternate, simple, semi-evergreen. Large and dark green. Glabrous and lustrous above. Paler beneath, lightly pubescent to glabrate. Susceptible to Lace bugs.

*Size.*—When fully expanded is 2½–4 inches long by ¾–1½ inch wide, larger than species.

*Shape.*—Elliptic to obovate.

*Apex.*—Acute.

*Base.*—Obtuse.

*Margin.*—Entire or shallowly lobed with soft spins, usually revolute.

*Venation.*—Prominent mid-rib. Lower side of mid-rib protrudes out from the lower leaf surface.

*Petiole.*—⅛ inch long on new-fully expanded leaves with red (R.H.S. 46A) color.

*Color.*—Dark green (R.H.S. 147A) upper surface, light green (R.H.S. 147C) lower surface for mature leaves and (R.H.S. 144A) upper surface, (R.H.S. 148C) lower surface for new leaves.

Stems:

*Strength.*—Young stems less than one year old, are stout, strong and approximately ⅛ to 3⁄16 inches in diameter.

*Color.*—Newly emerging stems 1⁄16 inch in diameter take on a reddish cast on the shaded side (R.H.S. 46A), then revert to grey-brown (R.H.S. 199C) once reach ⅛ inch size.

*Pith.*—Uniform on all aged wood.

Leaf buds: Rounded, 1⁄32 to 1⁄16 inch long, with imbricate scales having a color of greyed purple (R.H.S. 183B).

Flowers and fruit: As no mature specimen of this new tree exists, flowers and fruit have not yet been observed.

I claim:

1. A new and distinct variety of Southern Live Oak tree as herein described and illustrated, primarily characterized by the dominant central leader with strong branching angles, large dark green leaves, fast growth rate and thick trunk, branch and stem caliper.

* * * * *